(12) United States Patent
Motamedi et al.

(10) Patent No.: US 6,947,147 B2
(45) Date of Patent: Sep. 20, 2005

(54) DE-EMBEDMENT OF OPTICAL COMPONENT CHARACTERISTICS AND CALIBRATION OF OPTICAL RECEIVERS USING RAYLEIGH BACKSCATTER

(75) Inventors: Ali R. Motamedi, Los Altos, CA (US); Douglas M. Baney, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 361 days.

(21) Appl. No.: 10/225,512

(22) Filed: Aug. 21, 2002

(65) Prior Publication Data

US 2004/0036886 A1 Feb. 26, 2004

(51) Int. Cl.[7] ................................................. G01B 9/02
(52) U.S. Cl. ...................................... 356/479; 356/73.1
(58) Field of Search ................................ 356/477, 479, 356/484, 73.1; 250/227.19, 227.27; 385/12

(56) References Cited

U.S. PATENT DOCUMENTS

| | | | | |
|---|---|---|---|---|
| 5,202,745 A | * | 4/1993 | Sorin et al. ................ | 356/73.1 |
| 5,268,741 A | | 12/1993 | Chou et al. | |
| 5,365,335 A | | 11/1994 | Sorin | |

FOREIGN PATENT DOCUMENTS

| | | |
|---|---|---|
| EP | 0348235 A2 | 12/1989 |
| EP | 0453176 A2 | 11/1991 |
| EP | 0872721 A1 | 2/1998 |

OTHER PUBLICATIONS

Copy of European search report dated: Mar. 10, 2005.
Venkatesh et al., "Phase Noise Considerations in Coherent Optical FMCW Reflectometry", Journal of Lightwave Technology, vol. 11, No. 10, Oct. '93, pp. 1694–1700.
Oberson, et al., "Optical Frequency Domain Reflectometry with a Narrow Linewidth Fiber Laser", IEEE Photonics Technology Letters, vol. 12, No. 7, Jul. '00, pp. 867–869.
Huttner, et al., "Local Birefringence Measurements in Single–Mode Fibers with Coherent Optical Frequency–Domain Reflectometry", IEEE Photonics Technology Letters, vol., 10, No. 10, Oct. '98, pp. 1458–1460.
Bebbington et al., "Analytical Description of Backscattered States of Polarization in Polarization Optical Time–Domain Reflectometry Measurements on Uniformly Twisted Linearly Birefringent Optical Fiber", J. Opt. Soc. Am. A, vol. 17, No. 12, Dec. '00, pp. 2260–2266.
Shimizu et al., "Measurement of Rayleigh Backscattering in Single–Mode Fibers Based on Coherent OFDR Employing a DFB Laser Diode", IEEE Transactions Photonics Technology Letters, vol. 3, No. 11, Nov. '91, pp. 1039–1041.
Mermelstein et al., "Rayleigh Scattering Optical Frequency Correlation in a Single–Mode Optical Fiber", Optics Letters, vol. 26, No. 2, Jan. '01, pp. 58–60.
Passy et al., "Experimental and Theoretical Investigations of Coherent OFDR with Semiconductor Laser Sources", Journal of Lightwave Technology, vol. 12, No. 9, Sep. '94, pp. 1622–1630.

(Continued)

*Primary Examiner*—Samuel A. Turner

(57) ABSTRACT

Method and system are disclosed for de-embedding optical component characteristics from optical device measurements. In particular, the invention uses frequency domain averaging of the RBS on both sides of an optical component to determine one or more of its optical characteristics. Where the RBS has a slope (e.g., as in the case of a lossy fiber), a frequency domain least square fit can be used to determine the optical component characteristics. In addition, the invention uses a reference DUT to correct for variations in the frequency response of the photoreceiver. A reference interferometer is used in the invention to correct for sweep non-linearity of the TLS. The optical component characteristics are then de-embedded from optical device measurements to provide a more precise analysis of the optical device.

40 Claims, 8 Drawing Sheets

OTHER PUBLICATIONS

Tsuji, et al., "Coherent Optical Frequency Domain Reflectometry Using Phase–Decorrelated Reflected and Reference Lightwaves", Journal of Lightwave Technology, vol. 15, No. 7, Jul. '97, pp. 1102–1109.

von der Weid, et al., "On the Characterization of Optical Fiber Network Components with Optical Frequency Domain Reflectometry", Journal of Lightwave Technology, vol. 15, No. 7, Jul. '97, pp. 1131–1141.

* cited by examiner

DE-EMBEDMENT OF OPTICAL COMPONENT CHARACTERISTICS AND CALIBRATION OF OPTICAL RECEIVERS USING RAYLEIGH BACKSCATTER

BACKGROUND OF THE INVENTION

1. Technical Field of the Invention

The present invention is related to the de-embedding of optical component characteristics from optical device measurements and, in particular, to a method and system for de-embedding the optical component characteristics using Rayleigh backscatter.

2. Background of the Invention

Ideally, an optical signal entering one side of an optical component such as a connector or splice emerges from the other side at the same signal level. In actuality, however, some loss in signal strength will be incurred. Therefore, when analyzing an optical device, it is important to first de-embed the signal loss or other characteristics of any optical components that may be present.

Rayleigh backscatter (RBS) measurements can be used for de-embedding optical component characteristics such as signal loss. When measuring RBS, the level of RBS can be expressed in terms of the reflectivity RBS of the optical fiber as follows.

$$R_{RBS} = S \cdot \alpha \cdot \Delta z \quad (1)$$

where S is the RBS capture ratio, $\alpha$ is the attenuation coefficient due to the RBS, and $\Delta z$ is the spatial resolution of the RBS measurements. The capture ratio S and the attenuation coefficient $\alpha$ are characteristics of the optical fiber.

The spatial resolution $\Delta z$, on the other hand, is partly a function of the frequency span of the optical signal. In heterodyne measurement techniques, the best spatial resolution theoretically possible is given by:

$$\Delta z = \frac{c}{2 n_g \Delta \upsilon} \quad (2)$$

where c is the speed of light in a vacuum, $n_g$ is the group index of the fiber, and $\Delta \upsilon$ is the total frequency span of the optical signal. Thus, by expanding the frequency span $\Delta \upsilon$, the spatial resolution of the RBS measurements may be improved Unfortunately, using interferometic measurement techniques, the detected RBS has a noise like behavior that exists at all input power levels This noise like behavior makes it difficult to determine the difference in the level of RBS from one side of the optical component to the other. To compensate for this noise like behavior and to determine the RBS level accurately, the RBS signal must be averaged over the length of a fiber. Various time-domain averaging techniques have been used to compensate for the noise like behavior and also to improve the measurement dynamic range. However, these techniques cannot be used to directly measure optical component characteristics such as connector loss.

Another challenge in making RBS measurements using interferometic measurement techniques is to ensure that the magnitude response of the photoreceiver is flat over the desired frequency range. Non-linearity in the photoreceiver response results in variations in the photoreceiver output that prevent an accurate measurement of the RBS levels.

It is also important to ensure that the input optical signal is swept at a constant rate. A constant sweep rate means that the frequency of the input optical signal, typically from a tunable laser source (TLS), is changed at a constant rate. A non-constant sweep rate can broaden the beat frequency of the reflections that form RBS. Such broadening can make it very difficult to detect individual, closely-spaced reflections Because of the above difficulties in making RBS measurements, optical components characteristics measured based on RBS are sometimes inaccurate. As a result, the optical component characteristics can be incorrectly de-embedded from the optical device measurements. Accordingly, it would be desirable to provide a way to improve the accuracy of RBS based optical component characteristic measurements More specifically, it would be desirable to be able to compensate for the noise like behavior of the RBS signals, and to correct for any frequency response non-linearity in the photoreceiver, as well as any non-constant sweep rate in the TLS.

SUMMARY OF THE INVENTION

The invention is directed to a method and system for de-embedding optical component characteristics from optical device measurements. In particular, the invention uses frequency domain averaging of the RBS on both sides of an optical component to determine one or more of its optical characteristics The number of RBS data points available for averaging can be increased by expanding the averaging windows to include a larger portion of the RBS. Alternatively, the number of data points available for averaging can be increased by expanding the wavelength range of the TLS while keeping the measurement windows fixed. Where the RBS has a slope (e.g., as in the case of a lossy fiber), a frequency domain least square fit can be used to determine the optical component characteristics. In addition, the invention uses a reference DUT to correct for variations in the frequency response of the photoreceiver. A reference interferometer is used in the invention to correct for sweep non-linearity of the TLS. The optical component characteristics are then de-embedded from optical device measurements to provide a more precise analysis of the optical device.

As such, the invention is able to overcome the limitations and drawbacks of prior solutions by improving the accuracy of RBS measurements, and also correcting for any non-linearity in the photoreceiver and/or the TLS.

BRIEF DESCRIPTION OF THE DRAWINGS

The disclosed invention will be described with reference to the accompanying drawings, which show important exemplary embodiments of the invention and which are incorporated in the specification hereof by reference, wherein.

DETAILED DESCRIPTION OF EXEMPLARY EMBODIMENTS OF THE INVENTION

Embodiments of the invention provide a system and method for making more accurate optical component characteristic measurements using RBS The optical component characteristics can then be de-embedded from optical device measurements to provide a more precise analysis of the optical device. The accuracy of the optical component characteristic measurements can be improved by improving the accuracy of the RBS measurements. The accuracy of the RBS measurements, in turn, can be improved by frequency domain averaging of the RBS within a predefined window on both sides of the optical component. The averaged RBS may then be used to more precisely determine the RBS level on either side of the optical component In some embodiments of the invention, the averaging windows can be expanded in order to increase the number of data points available for averaging. In some embodiments of the invention, the number of data points available for averaging can be increased by expanding the sweep wavelength range while keeping the measurement window fixed Where the RBS level on either side of the optical component is sloped, a frequency domain least square fit may be applied to the RBS. The optical component characteristics may then be determined from the difference in the Y-axis intercepts of the resulting curves.

Although the invention is described herein with respect to Optical Frequency Domain Reflectometry (OFDR), other reflectometry techniques may certainly be used, such as Optical Time Domain Reflectometry (OTDR), and the like. In general, sweeping over a wide wavelength range in OFDR results in substantially the same spatial resolution as using a short pulse in OTDR. In addition, although the invention is described primarily with respect to measurement of transmission loss, other optical component characteristics may also be measured. For example, the invention may be applied to measurements of optical reflectivity, dispersion, and other characteristics of the optical component. Furthermore, the invention may be applied to various types of optical components including, but not limited to, optical connectors, splices, optical filters, multiplexers, combiners, and the like. Following is a description of the invention as it pertains to the de-embedding of signal loss due to an optical connector.

Figure 1:
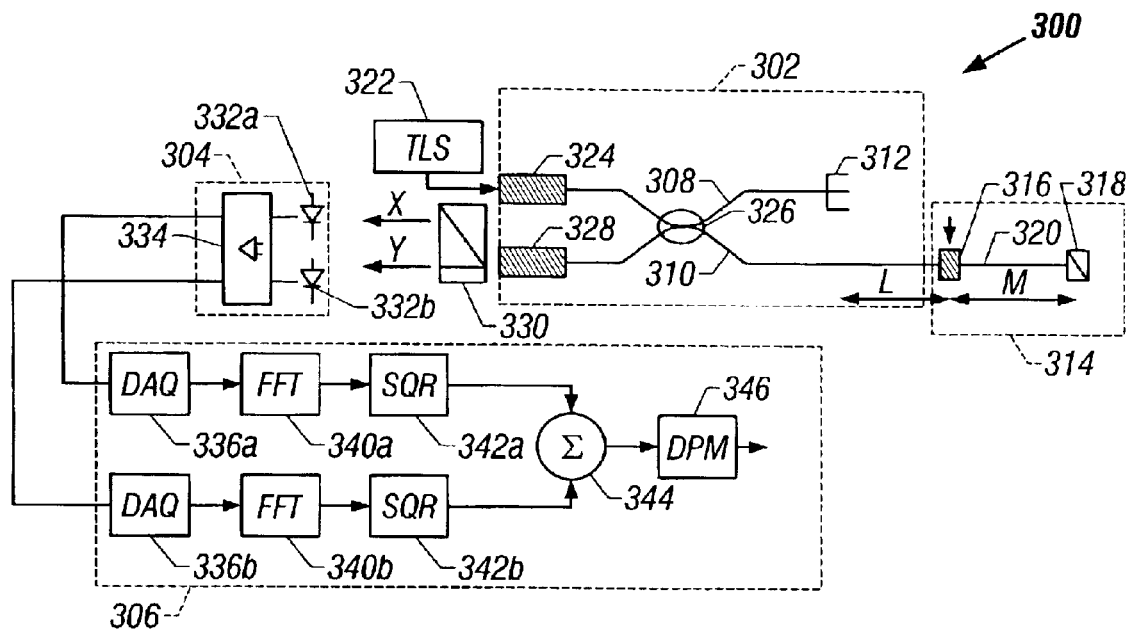
FIG. 1 illustrates an exemplary optical device analyzer according to embodiments of the invention.

Referring now to FIG. 1, an optical device analyzer 300 according to one exemplary embodiment of the invention is shown. Note that the term "device" as used herein may refer to a single optical component, or to several optical components connected together. In some embodiments, the optical device analyzer 300 is an optical interferometric (heterodyne) optical device analyzer The optical device analyzer 300 includes an interferometer 302, a polarization diversity photoreceiver 304, and a signal processing unit 306. The interferometer 302 includes two arms a reference arm 308, and a test arm 310. The reference arm 308 is terminated by a mirror 312, while the test arm 310 is terminated by a DUT 314

The DUT 314, in this case, includes an M-length optical fiber 320 that is to be characterized, although other optical devices may certainly be used. Leading up to the optical fiber 320 is a connector 316 (indicated by the arrow), the transmission loss from which needs to be de-embedded from the measurements of the optical fiber 320. A second connector 318 is connected to the opposite end of the optical fiber 320 that may be used, for example, to connect additional optical devices to the DUT 314. Note that the first connector 316 is located further down the test arm 310 by a distance L compared to the mirror 312.

A TLS 322 provides an optical signal that is swept over a wavelength (hence, frequency) range of interest. The wavelength range of interest may be, for example, 1550–1560 nm at a sweep rate of 40 nm/s. An optical isolator 324 is connected to the reference arm 308 of the interferometer 302. The isolator 324 serves to isolate the TLS 322 from the interferometer 302 in order to prevent any reflection of the optical signal from traveling back to the TLS 322. An optical coupler 326 divides the optical signal into the test arm 310 and the reference arm 308. The optical coupler 326 also combines any reflected portions of the optical signal traveling back along the two arms 308 and 310. The composite signal is provided to a second isolator 328 that is connected to the test arm 310. The second isolator 328 serves to isolate the interferometer 302 from the photoreceiver section of the heterodyne optical device analyzer 300.

Due to inhomogeneities in the optical fibers, a certain level of RBS will be generated along the optical fibers up to the second connector 318. One way to measure the level of RBS is to first split the composite signal into its various polarization components. Accordingly, in some embodiments of the invention, the composite signal is provided to an optical polarizing beam splitter 330 (through the second isolator 328). The optical polarizing beam splitter 330 may be any optical polarizing beam splitter such as a rutile crystal that splits light into orthogonal polarization components. For convenience purposes, the polarization components will be referred to herein as X-polarized and Y-polarized components. Thus, in the exemplary embodiment of FIG. 1, the optical polarizing beam splitter 330 splits the composite signal into X-polarized and Y-polarized components. The X-polarized and Y-polarized components of the composite signal are subsequently provided to the polarization diversity photoreceiver 304.

The polarization diversity photoreceiver 304 contains a number of optical components including photodetectors 332a and 332b. The photodetectors 332a and 332b may be photodiodes, for example. Each polarized component of the RBS is incident on a separate photodetector. For example, the X-polarized RBS component is incident on the first photodetector 332a, and the Y-polarized RBS component is incident on the second photodetector 332b. The photodetectors 332a and 332b output photocurrents that have beat signals with phase and magnitude which comprise the phase and magnitude of the signals from the DUT, including the reflected signals, such as RBS. The photocurrents may thereafter be enhanced through additional photoreceiver functions such as filtering, amplifying, and the like (shown generally at 334). Output signals representing a respective one of the polarized RBS components from the photoreceiver 304 are then provided to the signal processing unit 306 for further processing.

The signal processing unit 306 has a number of functional components including data acquisition modules 336a and 336b. The data acquisition modules 336a and 336b are configured to capture the X-polarized and Y-polarized components of the composite signal, respectively. More specifically, the data acquisition modules 336a and 336b detect the output signals from the photoreceiver 304 and convert the signals from analog to digital signals In this regard, the data acquisition modules may be implemented in some embodiments as a combination of hardware (e g, data acquisition cards) and software.

The signal processing unit 306 further includes Fourier transform modules 340a and 340b. The Fourier transform modules 340a and 340b are configured to transform the digital data representing the X-polarized and Y-polarized components from the time domain to the frequency domain. Such a conversion facilitates the analysis and processing of the data in the frequency domain. The type of Fourier transform used in the exemplary embodiment of FIG. 1 is a Fast Fourier Transform (FFT), although other types of Fourier transforms (e.g., discrete Fourier transform) may certainly be used.

The foregoing description assumes that the signal from the TLS 322 has a 45 degree polarization when it reaches the optical coupler. That is to say, the resulting X-polarized and Y-polarized components are assumed to have substantially equal magnitudes. Where the signal from the TLS has varying polarization, the polarization will need to be tracked and corrected or compensated so that the polarization components are substantially equal in magnitudes. The correction may be performed by the signal processing unit 306 in a manner known to those skilled in the art. Preferably, the correction is performed prior to the Fourier transform modules 340a and 340b.

The transformed data representing the X-polarized and Y-polarized components are provided to squaring modules 342a and 342b, respectively, after correcting for polarization (if needed) The function of the squaring modules 342a and 342b is to square (e.g., $x^2$) the magnitude of the data. The respective outputs of the squaring modules 342a and 342b are subsequently provided to a summing node 344 that is configured to add the squared X-polarized and Y-polarized components together. The squaring and summing of the X-polarized and Y-polarized components provides a polarization diverse signal. The result is an RBS waveform that is similar to the RBS waveform shown in FIG. 2.

Figure 2:
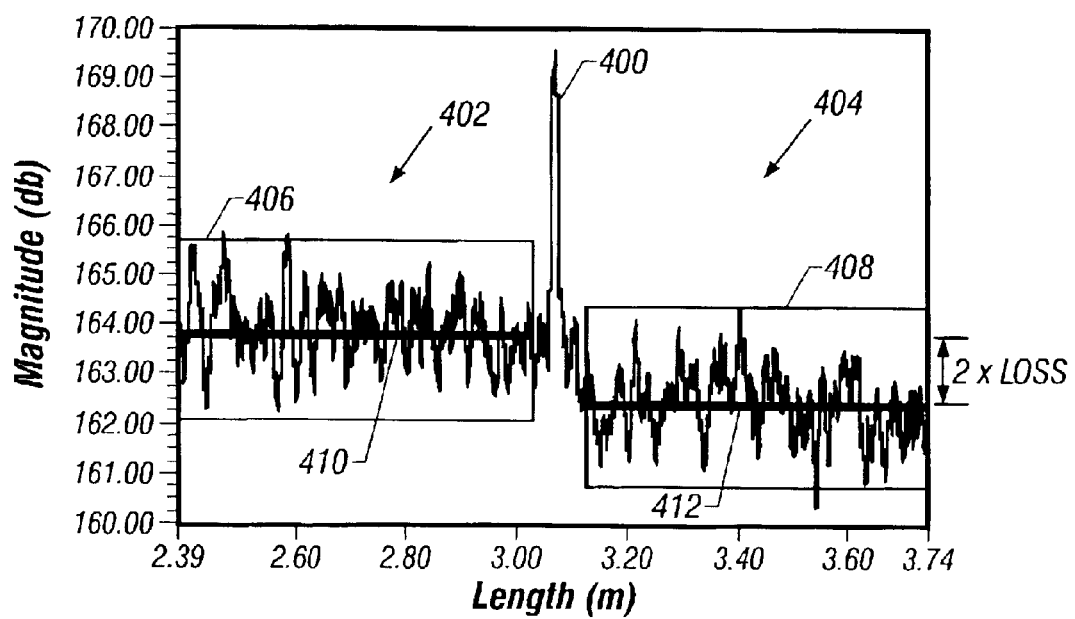
FIG. 2 illustrates an example of Rayleigh backscatter measured using the optical device analyzer according to embodiments of the invention.

In the chart of FIG. 2, the vertical axis represents the magnitude of the RBS, while the horizontal axis represents the length along the optical fiber up to and after the connector 316. The spike 400 in the middle of the chart represents the beat frequency that is due to the connector 316. The noise like signals 402 on the left-hand side of the spike 400 represent the RBS in the optical fiber before the connector 316. The noise like signals 404 on the right-hand side of the spike 400 represent the RBS in the optical fiber after the connector 316. As can be seen, there is a small drop in the RBS level on the right-hand side of the spike 400 compared to the RBS level on the left-hand side. This change in the RBS level represents twice the signal loss due to the connector 316, which loss can be expressed as follows:

$$\text{connector loss (dB)} = \frac{\Delta R_{RBS}(\text{dB})}{2} \quad (3)$$

However, because of the noise like behavior of the RBS, it is often difficult to accurately determine the magnitude of the change without some kind of averaging. Therefore, in accordance with the teachings and principles of the invention, the signal processing unit 306 further includes a data processing module 346 that is capable of averaging the RBS. The data processing module 346 performs the task of averaging using the data from the summing node 344. Because this data was previously transformed from the time domain to the frequency domain, the averaging is performed on the frequency content of the RBS More specifically, the averaging is performed using the magnitude associated with each of the frequencies in the RBS.

As can be seen from FIG. 2, a data window 406 is defined around a certain range of frequencies to the left of the spike 400. A similar data window 408 is also defined around a certain range of frequencies to the right of the spike 400. The RBS level associated with each frequency contained in the data windows 406 and 408 are subsequently averaged. The resulting averaged value 410 for the left-hand window 406 is indicated by the horizontal line in the middle of the window Likewise, the resulting average value 412 for the right-hand window 408 is indicated by the horizontal line in the middle of that window. The change in the RBS levels can now be determined simply by subtracting the two averages 410 and 412. The resulting difference will be twice the connector loss.

Figure 3:
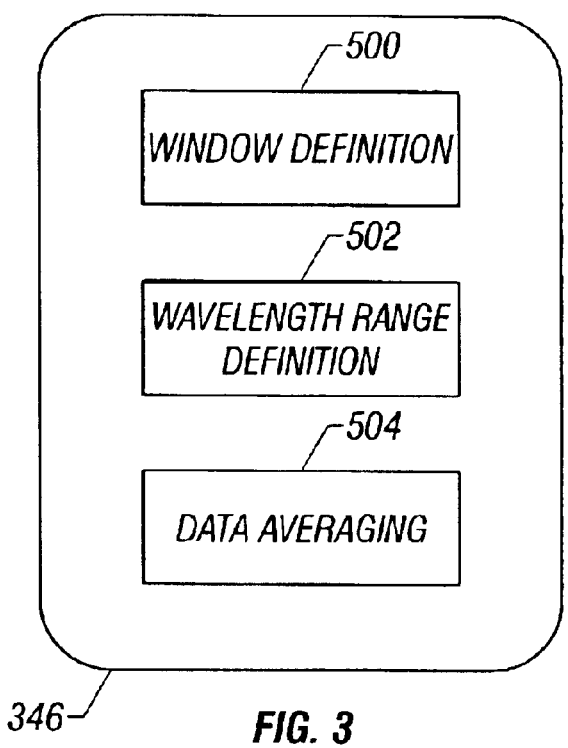
FIG. 3 illustrates a data processing module according to embodiments of the invention.

FIG. 3 illustrates the data processing module 346 in more detail. The data processing module 346 has a number of functional components including a window definition component 500. The window definition component 500 is configured to allow a user to manually define the size of the data windows 406 and 408 (see FIG. 2) The window size should be sufficiently large to include enough data points to ensure accurate approximation of the averaged RBS level. Generally, a higher number of data points will result in more accurate approximations. The number of data points that are available for averaging may be increased by expanding the size of the data window. The size of the data window should not be expanded so far, however, that it includes adjacent components, such as the second connector 318.

Alternatively, the window definition component 500 may be configured to determine the size of the data windows 406 and 408. The size of the data windows 406 and 408 may be determined based on one or more predefined criteria. Such predefined criteria may include, for example, minimum number of data points, optimum number of data points, or other similar criterion. For a given spatial resolution $\Delta z$, the number of data points in a window depends on the size of the window. This relationship can be expressed as $$\text{\# data pts} = \frac{\text{window size}}{\Delta z} \quad (4)$$

Using this relationship, the window definition component 500 may adjust the data window 406 and 408 until a certain specified number of data points is satisfied. For example, a window size of 56 cm may be sufficient to satisfy a certain data point requirement for a spatial resolution of 69 $\mu$m.

Of course, higher spatial resolutions will result in more data points and more accurate approximations than lower spatial resolutions for the same size window Thus, where the size of the data window must remain fixed or where expansion is limited (e.g., due to the location of an adjacent connector), the number of data points may be increased by increasing the spatial resolution $\Delta z$. Recall from Equation (2) that the spatial resolution $\Delta z$ of the RBS measurements depends, in part, on the frequency span $\Delta v$ of the optical signal. Accordingly, by expanding the wavelength range (hence, frequency span), the spatial resolution, and thus, the number of data points for a given size window may be increased.

Although the above discussion is with respect to OFDR, a similar outcome may be obtained with OTDR. Recall that sweeping over a wide wavelength range in OFDR results in substantially the same spatial resolution as using a short pulse in OTDR The frequency span may be expanded by expanding the sweep wavelength range of the TLS. Thus, in some embodiments, the data processing module further includes a sweep wavelength range component 502. The sweep wavelength range component 502 is configured to determine the approximate sweep wavelength range required to obtain a certain spatial resolution for a given size window. In some embodiments, the sweep wavelength range component 502 uses Equation (2) to calculate a frequency span (hence, wavelength range) that would be needed to obtain the desired spatial resolution for a given size window. An increase in the sweep wavelength range increases the spatial resolution, which increases the number of data points available in a given size window for averaging.

Averaging of the RBS is performed by the data averaging module 504. In some embodiments, the averaging module 504 determines a statistical mean for the average values 410 and 412 (see FIG. 2) for the data points in each data window 406 and 408. The data averaging module 504 thereafter subtracts the average values 410 and 412 from one another to approximate the connector loss. In some embodiments, the average values 410 and 412 may be determined based on a single waveform, or trace, of the RBS captured by the signal processing unit 306 Alternatively, the average values 410 and 412 for each data window 406 and 408 in multiple traces may be determined. A total average value for each window 406 and 408 may then be calculated from the average values for all the multiple traces In still other embodiments, instead of using a statistical mean, the data averaging module 504 may determine the connector loss using some other mathematical model. For example, the data averaging module 504 may apply a least square fit to the RBS where the level of the RBS on either side of the connector is sloped (i.e., non-flat). The Y-axis intercepts of the resulting curves in dB may then be subtracted from one another to approximate the connector loss.

Once the average values 410 and 412 have been determined, the data averaging module is configured to determine the connector loss using, for example, Equation (3) above. The data averaging module thereafter de-embeds the connector loss from any optical device measurements made using the connector by, for example, subtracting the connector loss from the optical device measurements.

To further improve the accuracy of the RBS measurements, correction for photoreceiver frequency response non-linearity may be performed As alluded to earlier, one of the challenges in making RBS measurements is to ensure the flatness of the photoreceiver frequency response over a large frequency span. Any deviation from a flat photoreceiver response may result in slopes or other variations in the measured RBS level. One way to correct for these variations versus frequency is to measure the RBS using a DUT that is known to have very little or no loss. Any slope or variation in the measured RBS level may then be attributable solely to the photoreceiver. The slopes or variations in the RBS level from the known DUT may then be subtracted from the measured RBS level from the unknown DUT to correct for the photoreceiver frequency response non-linearity. This correction of the photoreceiver frequency response non-linearity is described in more detail below with the aid of FIGS. 4–7.

Figure 4:
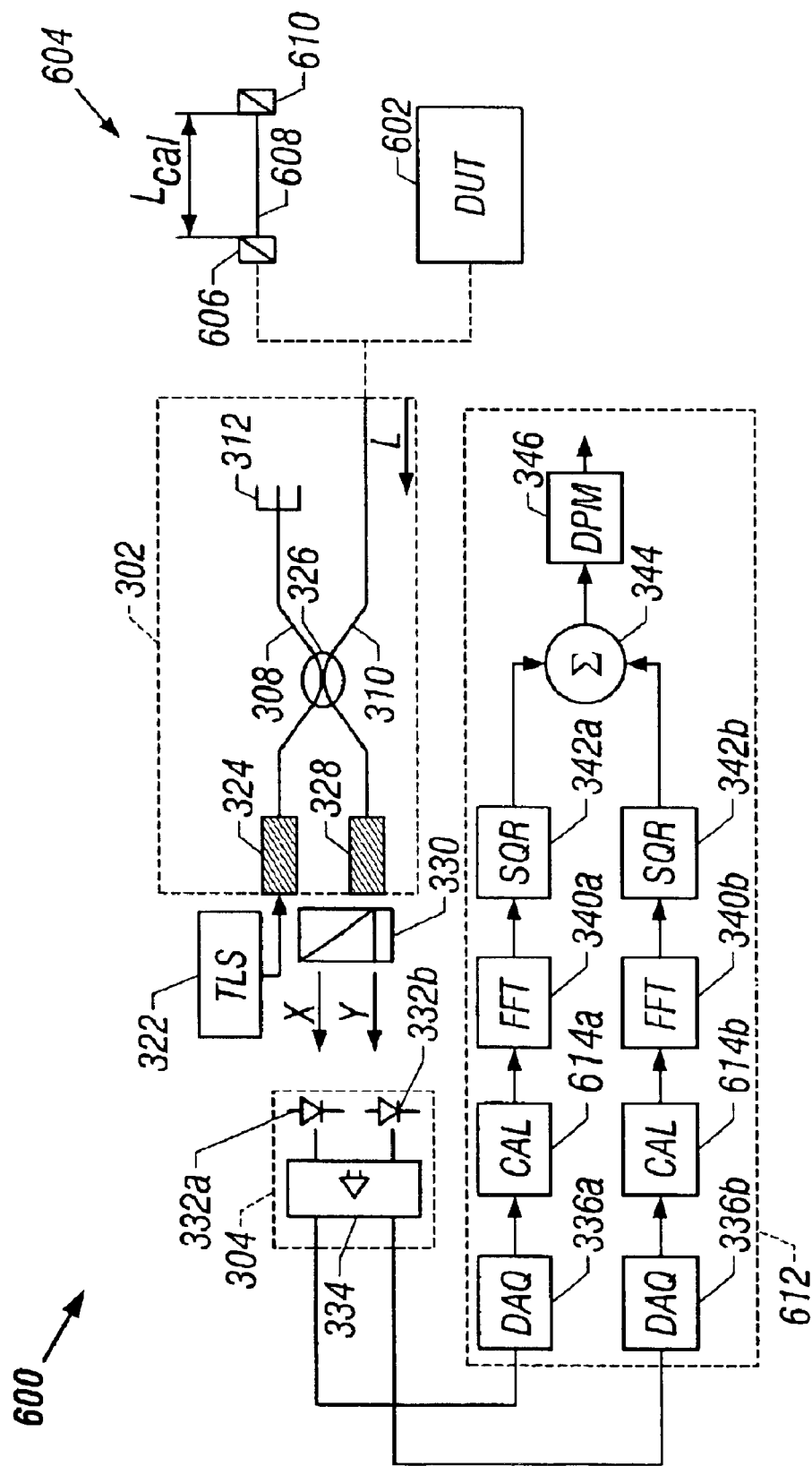
FIG. 4 illustrates an exemplary optical device analyzer set up to correct photoreceiver frequency response non-linearity according to embodiments of the invention.

FIG. 4 illustrates an optical device analyzer 600 that can be used to correct for the photo photoreceiver frequency response variations. The optical device analyzer 600 is similar to the one shown in FIG. 1 in that it includes the interferometer 302 and the photoreceiver 304. The TLS 322 and the optical polarizing beam splitter 330 are also present, but the DUT 314 has been replaced by an unknown DUT 602 and a known DUT 604. The known DUT 604 preferably includes an optical device such as a length of optical fiber 608 that has very little or no loss. A connector 606 connects one end of the optical fiber 608 to the interferometer 302. A second connector 610 terminates the other end of the optical fiber 608.

The length of the optical fiber 608 should be long enough such that the largest beat frequency therefrom will be at the upper cut-off frequency of the photoreceiver 304. This length can be calculated from the following equation:

$$L_{cal} = \frac{c}{n_g} \Delta T \frac{f_b}{F_s} \qquad (4)$$

where c is the speed of light in a vacuum, $n_g$ is the group index of transmission medium (in this case, fiber), $\Delta T$ is the total measurement time, $f_b$ is the highest beat frequency of interest, and $F_s$ is the total frequency span of the TLS 322.

In addition to the above, the optical device analyzer 600 further includes a signal processing unit 612. The signal processing unit 612 is otherwise similar to the signal processing unit 306 of FIG. 1 except for the presence of calibration modules 614a and 614b. The calibration modules 614a and 614b perform the task of correcting for photoreceiver frequency response non-linearity on the acquired data. This task may be performed either immediately after the data is acquired by the data acquisition modules 336a and 336b, or after some other task.

In operation, the unknown DUT 602 is disconnected from the interferometer 302, while the known DUT 604 is connected to the interferometer 302. The TLS 322 is then swept at the sweep rate of interest over the wavelength range of interest. The RBS from the known DUT 604 is acquired by the data acquisition modules 336a and 336b, then temporarily stored by the calibration modules 614a and 614b. The known DUT 604 is then disconnected from the interferometer 302, and the unknown DUT 602 is connected The RBS from the unknown DUT 602 is then acquired. The calibration modules 614a and 614b subsequently subtract any slopes or variations in the RBS measurements of the known DUT 604 from the RBS measurements of the unknown DUT 602. In this way, the RBS is corrected for any photoreceiver frequency response non-linearity. The corrected RBS may then be used by the data processing module 346 to determine an average value for the RBS.

Figure 5:
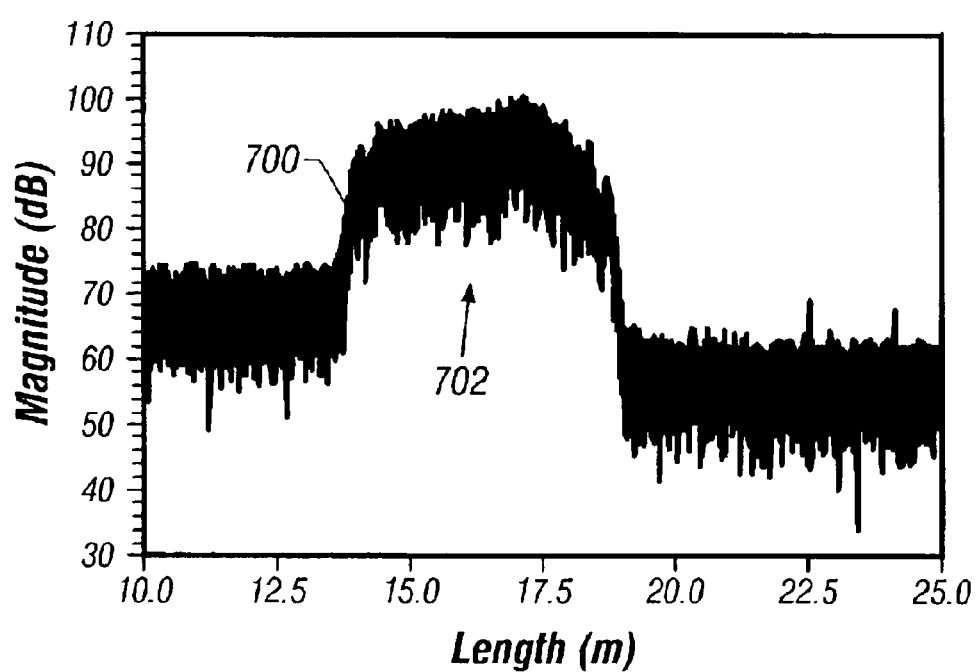
FIG. 5 illustrates an example of spreading due to non-linearity in the sweep rate of the TLS.

Non-linearity may also be present in the TLS, resulting in a non-constant sweep rate. Sweep non-linearity of the TLS causes spreading of the peaks that represent reflections in the optical fiber. For a single discontinuity or reflection, only a single beat frequency is expected according to Equation (1). However, due to sweep non-linearity of the TLS, the beat frequency may actually contain a spectrum of frequencies, as shown by the example in FIG. 5. Consequently, it can be very difficult to locate the true discontinuity or reflection accurately. Referring to FIG. 5, the vertical axis represents the magnitude of the reflections and the horizontal axis represents the length along the optical fiber The peak 700 has spread (indicated generally at 702) such that it is difficult to determine the precise peak location. One way to correct for sweep non-linearity is to track the sweep non-linearity of the TLS using a reference interferometer. The output of the reference interferometer may then be used to resample the output of the desired interferometer to correct for the sweep non-linearity.

Figure 6:
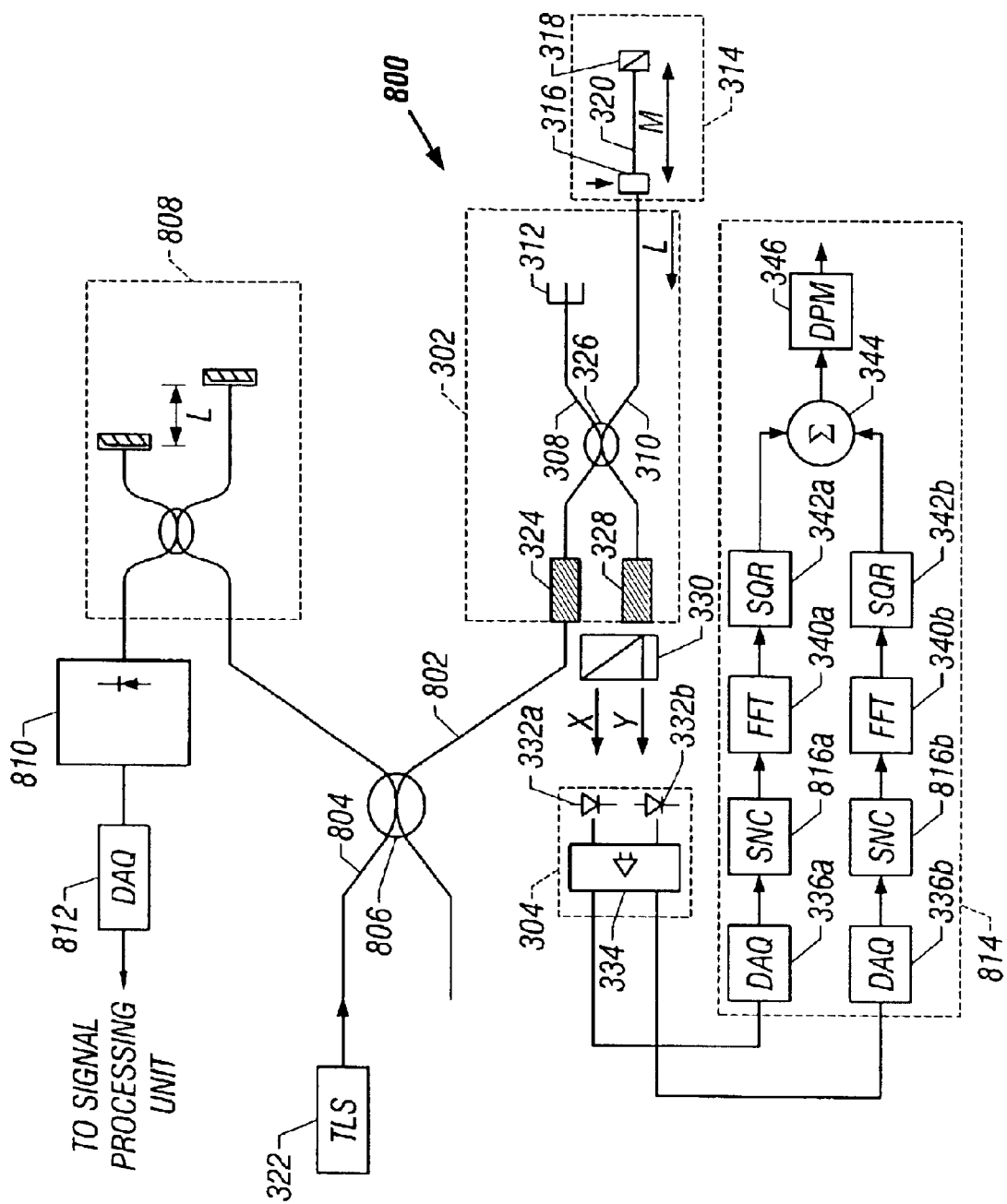
FIG. 6 illustrates an exemplary optical device analyzer set up to correct sweep rate non-linearity according to embodiments of the invention.

FIG. 6 illustrates an optical device analyzer 800 that is capable of correcting for sweep non-linearity in the TLS. The optical device analyzer 800 is similar to the one shown in FIG. 1 in that it includes the interferometer 302 and the photoreceiver 304. The DUT 314, the TLS 322, and the optical polarizing beam splitter 330 are also present. A length of optical fiber 802 carries the optical signal from the TLS 322 to the target interferometer 302. The optical fiber 802 is coupled to a second length of optical fiber 804 by an optical coupler 806. The optical coupler 806 divides the optical signal from the TLS 322 into the two lengths of optical fiber 802 and 804 The second optical fiber 804 then carries the optical signal to a reference interferometer 808 The reflected output of the reference interferometer 808 is provided to a photoreceiver 810, which may be a conventional photoreceiver similar to the one shown in FIG. 1. The output of the photoreceiver 810 is thereafter acquired by a data acquisition module 812, which may be a conventional data acquisition module similar to the ones shown in FIG. 1. In fact, in some embodiments, the data acquisition module 812 may be a part of the same physical data acquisition card as the data acquisition modules 336a and 336b of FIG. 1. The data from the data acquisition module 812 is then provided to a signal processing unit 814.

The signal processing unit 814 is similar to the signal processing unit 306 of FIG. 1 except for the presence of sweep non-linearity correction modules (SNC) 816a and 816b. The sweep non-linearity correction modules 816a and 816b perform the task of correcting for sweep non-linearity in the TLS 322. This task may be performed either immediately after the data is acquired by the data acquisition modules 336a and 336b, or after some other task.

In operation, an optical signal is swept at a desired sweep rate over a predefined wavelength range by the TLS 322. The optical signal is divided by the optical coupler 806 into the optical fiber 802 and 804. Because the signals originated from the same TLS 322, the divided signals will have identical sweep non-linearity (if any) relative to each other. The optical fiber 802 and 804 carry the divided optical signals to the target interferometer 302 and the reference interferometer 808, respectively A composite signal from the reference interferometer 808 is then provided to the photoreceiver 810, resulting in a beat signal having a number of beat frequencies. This beat signal is subsequently acquired by the data acquisition module 812 The acquired beat signal is then provided to the signal processing unit 814 where it is temporarily stored by the sweep non-linearity correction modules 816a and 816b At the same time, the RBS from the target interferometer 302 is acquired and provided to the signal processing unit 814. The sweep non-linearity correction modules 816a and 816b of the signal processing unit 814 corrects for the sweep non-linearity of the TLS 322.

Alternatively, instead of using the reference interferometer 806, a wavemeter may be used as a reference to detect sweep non-linearity in the TLS 322. The output of the wavemeter may be used by the sweep non-linearity correction modules 816a and 816b to correct for sweep non-linearity in the target interferometer 302.

Figure 7:
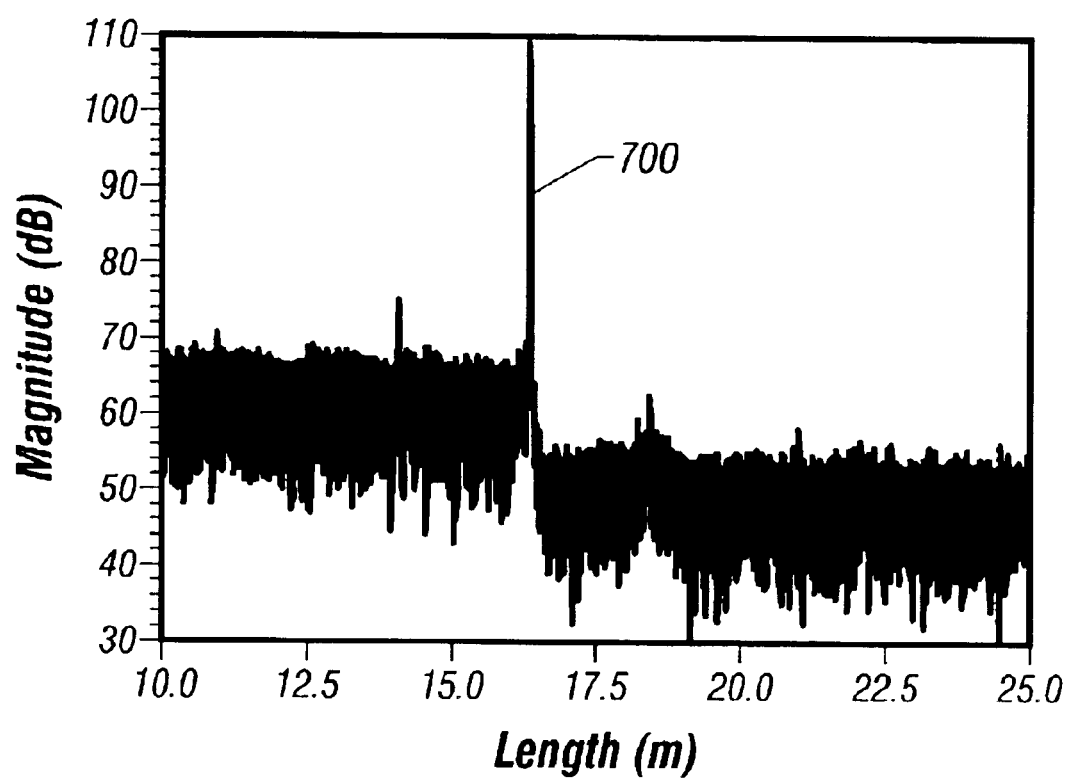
FIG. 7 illustrates an example of RBS measurements with correction for sweep rate non-linearity.

FIG. 7 illustrates a chart of the RBS measurements from the target interferometer 302. The chart in FIG. 7 is similar to the chart in FIG. 5, except the spreading 702 due to sweep non-linearity has been corrected. As a result, the peak 700 is now more clearly defined.

Figure 8:
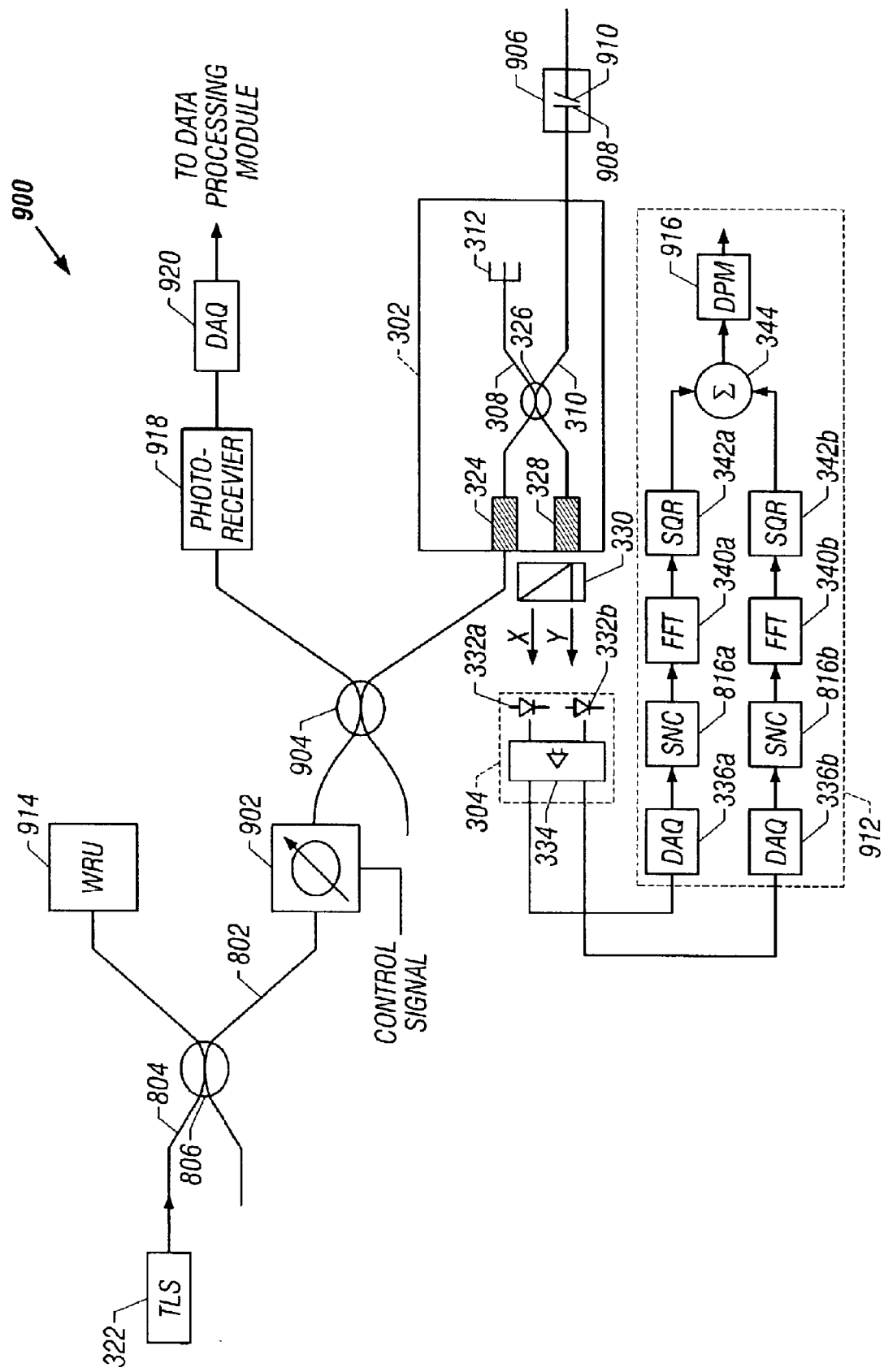
FIG. 8 illustrates an exemplary optical device analyzer set up to determine polarization dependent loss according to embodiments of the invention.

A common parameter that plays an important part in the performance of optical networks is polarization dependent loss (PDL). PDL can result from the use of angled-polished connectors to connect optical devices. Angled polished-connectors are often used because of their very low return loss. However, connecting an angled polished-connector to a flat connector can result in PDL levels that can adversely affect the overall performance of the optical network. Therefore, to be able to properly analyze a device, the PDL level of each optical component must be accurately de-embedded from device measurements. In accordance with embodiments of the invention, Rayleigh backscatter is used to measure the PDL levels FIG. 8 illustrates an exemplary optical device analyzer 900 for measuring PDL The optical device analyzer 900 is similar to the optical device analyzer 800 (see FIG. 6), except a polarizer 902 is used to vary the polarization of the optical signal from the TLS 322. The output of the polarizer 902 is then provided to the interferometer 302 through an optical coupler 904 A DUT 906 is connected to the test arm 310 of the interferometer 302. The DUT 906, in this case, includes two lengths of optical fibers. A flat polished connector 908 and an angled polished-connector 910 connect the two optical fibers together. The resulting composite signal from the interferometer 302 is provided to the optical polarizing beam splitter 330. The output of the optical polarizing beam splitter 330 is received by the polarization diverse receiver 304, and processed by a signal processing unit 912. A wavemeter 914 serves as a reference unit for purposes of correcting sweep non-linearity The wavemeter 914 performs substantially the same function as the reference interferometer 808 (see FIG. 6).

In operation, the polarizer 902 varies the polarization of the optical signal from the TLS 322. A control signal from, for example, the data processing module 916, increments the polarization state of the polarizer 902 for each sweep of the optical signal. When the optical signal passes through the angled polished-connector 908, a different amount of loss will be incurred for each polarization state The connector loss is measured by the signal processing unit 910 for each sweep. Specifically, a data processing module 916 of the signal processing unit 910 measures the connector loss using Rayleigh backscatter in a manner similar to that described previously with respect to FIG. 6. The data processing module 916 then determines the PDL by subtracting the minimum loss from the maximum loss The difference between the minimum and maximum losses is the PDL of the DUT 906.

The number of polarization states, hence sweeps, that is used can be selected as needed and should be sufficiently large to ensure an accurate maximum and minimum loss. Preferably, all possible polarization states are used for a given sweep wavelength range. In some embodiments, however, rather than stepping through a large number of polarization states, a Jones matrix, Mueller matrix, or the like may be used to determine the maximum and minimum losses In some embodiments, the data processing module 916 is further configured to determine the output power profile of the polarizer 902 for each polarization state Ideally, the output power of the polarizer 902 should be constant for all polarization states In actuality, however, the output power of the polarizer 902 will vary depending on the particular polarization state selected (due to variations in the polarization of the optical signal from the TLS 322).

To determine the output power profile, a photoreceiver 918 may be connected to the optical coupler 904. The photoreceiver 918 is similar to the photoreceiver 304 described previously, and is configured to receive the optical signal from the polarizer 902 via the optical coupler 904. The output of the photoreceiver 918 is then captured by a data acquisition unit 920. Data from the data acquisition unit 920 is thereafter provided to the data processing module 916. The data processing module 916 uses this data to determine the polarizer output power profile for each polarization state. The output power profile may then be used to adjust the RBS measurements for each polarization state, respectively. In this way, a more accurate PDL may be determined.

Figure 9A:
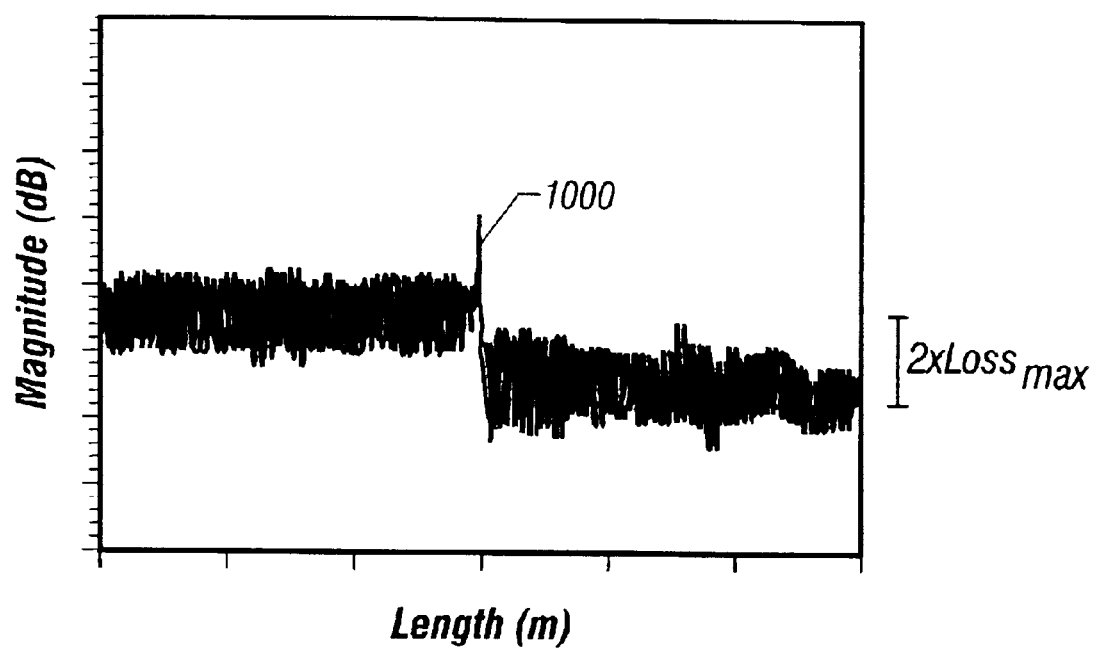
FIGS. 9A–B illustrate examples of RBS measurements used to determine polarization dependent loss according to embodiments of the invention.
Figure 9B:
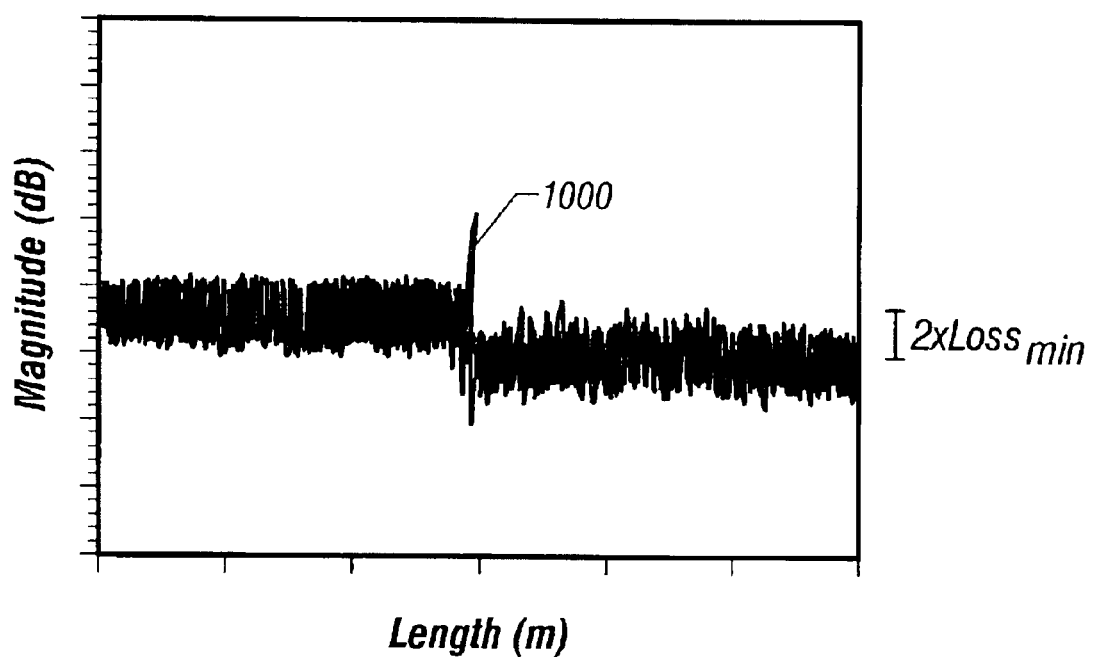

The PDL determination is graphically illustrated in FIGS. 9A–B, where two charts of the RBS measurements are shown. In FIGS. 9A–B, the vertical axis represents the magnitude of the reflections in dB and the horizontal axis represents the length along the optical fibers. The spike 1000 in the middle of each chart corresponds to the DUT 906. As can be seen, the difference in RBS levels in the top chart (FIG. 9A) represents two times the maximum loss determined by the data processing module 916. On the other hand, the difference in RBS levels in the bottom chart (FIG. 9B) represents two times the minimum loss determined by the data processing module 916. The PDL can then be determined as follows (in dB):

$$PDL = Loss_{max} - Loss_{min} \quad (5)$$

Figure 10A:
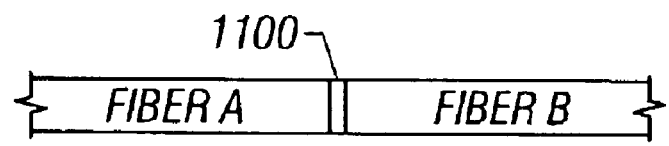
FIGS. 10A–10B illustrate two difference fiber types are connected to together and the RBS measurement resulting therefrom.
Figure 10B:
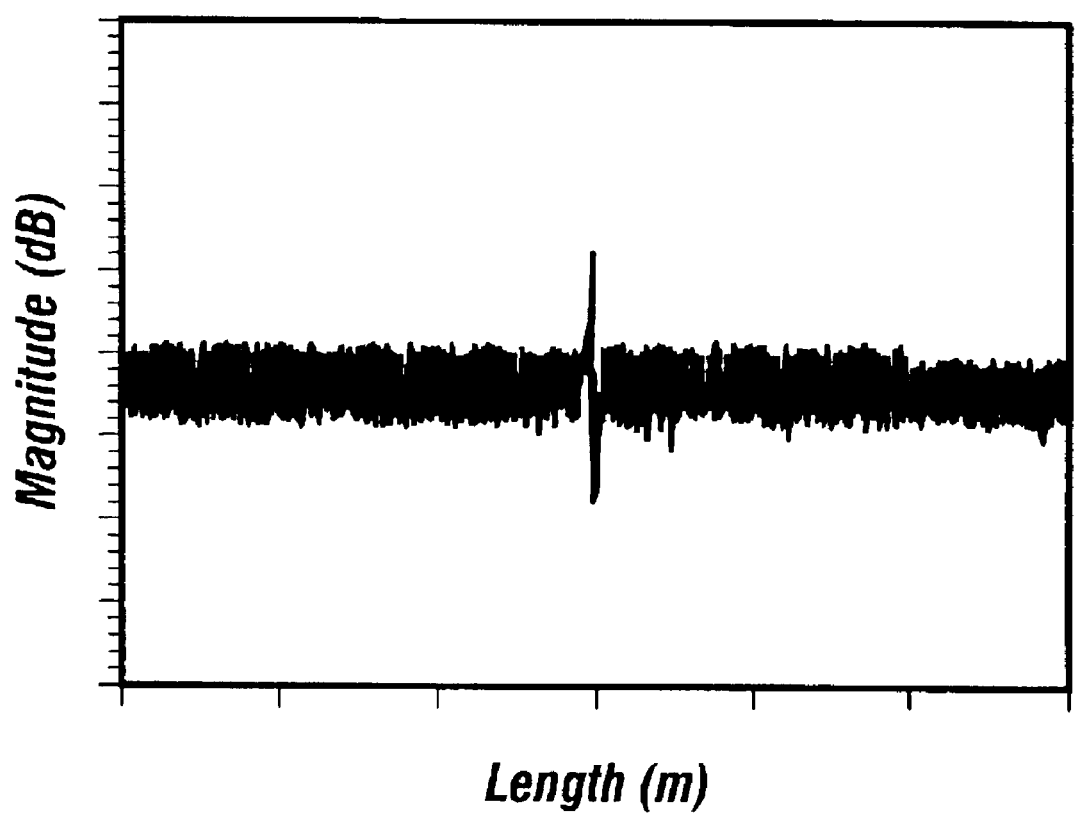

In addition, Rayleigh backscatter levels can vary depending on the type of fiber used, as indicated by Equation (1) above. Therefore, RBS levels that are measured without knowing the capture ratio S and the attenuation coefficient $\alpha$ of the fiber used may result in erroneous connector loss measurements This scenario is demonstrated in FIGS. 10A–B, where two different types of fibers, FIBER A and FIBER B, are used. The connector 1100 is known to have about 0.5 dB loss. However, the RBS level from FIBER B is about 1.0 dB higher than the RBS level from FIBER A. Therefore, a direct calculation of the connector loss using the RBS levels would erroneously result in a 0 dB loss through the connector, as shown in FIG. 10B.

In accordance with certain embodiments of the invention, a lookup table is used to store the parameters (e.g., S, $\alpha$, $R_{RBS}$) for different kinds of fibers The lookup table can reside, for example, in the signal processing unit 912 of the invention. The parameters in the lookup table can then be used by the data processing module 916 to calculate the appropriate RBS levels for each fiber type for a given spatial resolution using Equation (1). The calculated RBS levels may then be used to offset the measured RBS levels as needed. An exemplary lookup table is shown in Table 1 below. As can be seen, there is a 1.0 dB difference in RBS between FIBER A and FIBER B. Adjusting the measured RBS by 1.0 dB results in a connector loss of 0 5 dB

TABLE 1

| Fiber Type | S | $\alpha$ | $R_{RBS}$ (dB,) |
|---|---|---|---|
| A | S1 | $\alpha_1$ | −110 |
| B | S2 | $\alpha_2$ | −109 |
| C | S3 | $\alpha_3$ | −108 |

As will be recognized by those skilled in the art, the innovative concepts described in the present application can be modified and varied over a wide range of applications. For example, although the calibration modules and the sweep non-linearity correction modules have been shown independently from each other, in some embodiments, they both may be present in the same heterodyne optical device analyzer. Accordingly, the scope of patented subject matter should not be limited to any of the specific exemplary teachings discussed, but is instead defined by the following claims.

We claim:

1. A method of de-embedding optical component characteristics from optical device measurements using Rayleigh backscatter (RIBS), comprising:

sweeping an optical signal at a predefined sweep rate over a predefined wavelength range;

detecting the RBS on both sides of an optical component;

obtaining a frequency domain average or a frequency domain least square fit for the RBS on both sides of the optical component;

determining an optical component characteristic from the frequency domain average or the frequency domain least square fit; and de-embedding the optical component characteristic from the optical device measurements.

2. The method according to claim 1, wherein the RBS is detected using an optical interferometric analyzer.

3. The method according to claim 2, wherein the optical component characteristic includes a predetermined one of transmission loss, optical reflectivity, and dispersion.

4. The method according to claim 2, further comprising defining a data window around the RBS on both sides of the optical component, and adjusting a size of the data windows to increase the number of data points available for averaging.

5. The method according to claim 2, further comprising adjusting the wavelength range of the optical signal to increase a spatial resolution of the analyzer.

6. The method according to claim 2, further comprising correcting for photoreceiver frequency response variation using a reference device under test.

7. The method according to claim 2, further comprising correcting for sweep non-linearity in the RBS using a reference interferometer.

8. The method according to claim 1, further comprising varying a polarization state of the optical signal and determining an optical component characteristic for each polarization state.

9. The method according to claim 8, further comprising subtracting a minimum value of the optical component characteristic from a maximum value of the optical component characteristic to determine a polarization dependence of the optical component characteristic.

10. The method according to claim 9, wherein the minimum value and the maximum value of the optical component characteristic are determined using a preselected one of a Jones matrix and a Mueller matrix method.

11. The method according to claim 8, wherein the step of varying a polarization state is performed using a polarizer, further comprising determining an output power profile of the polarizer for each polarization state, and adjusting the optical component characteristic using the output power profile.

12. The method according to claim 1, further comprising storing information for different optical fibers in a lookup table, and using the information to adjust the optical component characteristic.

13. An optical device analyzer for use with an interferometer and a photoreceiver, the interferometer receiving an optical signal at a predefined sweep rate over a predefined wavelength range from an optical source, and the photoreceiver detecting RBS in a composite signal from the interferometer, comprising;
    a signal processing unit configured to capture RBS on both sides of an optical component from the photoreceiver and to transform the RBS from the time domain to the frequency domain; and
    a data processing module configured to determine a frequency domain average for the RBS or a frequency domain least square fit for the RBS.

14. The optical device analyzer according to claim 13, wherein the data processing module is further configured to determine an optical component characteristic based on the averaged RBS or the least square fit.

15. The optical device analyzer according to claim 13, wherein the optical component characteristic includes a predetermined one of transmission loss, optical reflectivity, and dispersion.

16. The optical device analyzer according to claim 13, wherein the data processing module is further configured to de-embed the optical component characteristic from optical device measurements that include the optical component characteristic.

17. The optical device analyzer according to claim 13, wherein the data processing module is further configured to define a data window around the RBS on both sides of the optical component, and to adjust a size of the data windows to increase the number of data points available for averaging.

18. The optical device analyzer according to claim 13, wherein the data processing module is further configured to adjust the wavelength range of the optical signal to increase a spatial resolution of the optical device analyzer.

19. The optical device analyzer according to claim 13, further comprising an optical polarizing beam splitter configured to split the composite signal into orthogonal polarization components.

20. The optical device analyzer according to claim 18, wherein the signal processing unit is further configured to square the polarization components and to add the squares to obtain a polarization-diverse signal.

21. The optical device analyzer according to claim 13, wherein the signal processing unit is further configured to correct for photoreceiver frequency response variation using a reference device under test.

22. The optical device analyzer according to claim 20, wherein the reference device under test is an optical fiber having a length such that the highest beat frequency resulting therefrom is at the upper cut-off frequency of the photoreceiver.

23. The optical device analyzer according to claim 13, wherein the signal processing unit is further configured to correct for sweep non-linearity in the optical source using a reference interferometer.

24. The optical device analyzer according to claim 13, wherein the signal processing unit is further configured to correct for sweep non-linearity in the optical source using a wave meter.

25. The optical device analyzer according to claim 13, wherein the optical device analyzer is an optical interferometric analyzer.

26. The optical device analyzer according to claim 13, further comprising a polarizer for varying a polarization state of the optical signal, wherein the data processing module is further configured to determine an optical component characteristic for each polarization state.

27. The optical device analyzer according to claim 25, wherein data processing module is configured to subtract a minimum value of the optical component characteristic from a maximum value of the optical component characteristic to determine a polarization dependence of the optical component characteristic.

28. The optical device analyzer according to claim 26, wherein the minimum value and the maximum value of the optical component characteristic are determined using a preselected one of a Jones matrix and a Mueller matrix method.

29. The optical device analyzer according to claim 25, wherein the data processing module is configured determine an output power profile of the polarizer for each polarization state, and to adjust the optical component characteristic using the output power profile.

30. The optical device analyzer according to claim 13, wherein the signal processing unit is further configured to store information regarding different optical fibers in a lookup table, and the data processing module is further configured to use the stored information to adjust the optical component characteristic.

31. A method of de-embedding optical component characteristics from optical device measurements using Rayleigh backscatter (RBS), comprising:
    sweeping an optical signal at a predefined sweep rate over a predefined wavelength range;
    detecting the RBS on both sides of an optical component using an interferometric analyzer;
    adjusting a wavelength range of the optical signal to increase a spatial resolution of the analyzer;
    obtaining a frequency domain average or a frequency domain least square fit for the RBS on both sides of the optical component;
    determining an optical component characteristic from the frequency domain average or the frequency domain least square fit; and
    de-embedding the optical component characteristic from the optical device measurements.

32. The method according to claim 30, wherein the optical component characteristic includes a predetermined one of transmission loss, optical reflectivity, and dispersion.

33. The method according to claim 30, further comprising defining a data window around the RBS on both sides of the optical component, and adjusting a size of the data windows to increase the number of data points available for averaging.

34. The method according to claim 30, further comprising correcting for photoreceiver frequency response variation using a reference device under test.

35. The method according to claim 30, further comprising correcting for sweep non-linearity in the RBS using a reference interferometer.

36. The method according to claim 30, further comprising varying a polarization state of the optical signal and determining an optical component characteristic for each polarization state.

37. The method according to claim 35, further comprising subtracting a minimum value of the optical component characteristic from a maximum value of the optical component characteristic to determine a polarization dependence of the optical component characteristic.

38. The method according to claim 36, wherein the minimum value and the maximum value of the optical component characteristic are determined using a preselected one of a Jones matrix and a Mueller matrix method.

39. The method according to claim 35, wherein the step of varying a polarization state is performed using a polarizer, further comprising determining an output power profile of the polarizer for each polarization state, and adjusting the optical component characteristic using the output power profile.

40. The method according to claim 32, further comprising storing information for different optical fibers in a lookup table, and using the information to adjust the optical component characteristic.

* * * * *

UNITED STATES PATENT AND TRADEMARK OFFICE
CERTIFICATE OF CORRECTION

PATENT NO.    : 6,947,147 B2
DATED         : September 20, 2005
INVENTOR(S)   : Motamedi et al.

It is certified that error appears in the above-identified patent and that said Letters Patent is hereby corrected as shown below:

Title page,
Item [56], References Cited, FOREIGN PATENT DOCUMENTS, delete "12/1989" and insert -- 06/1989 --.

Column 12,
Line 23, delete "(RIBS)" and insert -- (RBS) --.

Column 13,
Line 12, delete "intefferometer" and insert -- interferometer --.

Signed and Sealed this

Fourteenth Day of February, 2006

JON W. DUDAS
*Director of the United States Patent and Trademark Office*